US009717931B2

(12) United States Patent
Candau et al.

(10) Patent No.: US 9,717,931 B2
(45) Date of Patent: Aug. 1, 2017

(54) SOLUBILIZATION OF TRIAZINE UV-SCREENING AGENTS WITH ARYLALKYL BENZOATE COMPOUNDS/AMIDE-BASED OILS AND PHOTOPROTECTIVE COMPOSITIONS COMPRISED THEREOF

(75) Inventors: Didier Candau, Bievres (FR); Cecile Fiandino, Paris (FR)

(73) Assignee: L'Oreal, Paris (FR)

( * ) Notice: Subject to any disclaimer, the term of this patent is extended or adjusted under 35 U.S.C. 154(b) by 321 days.

(21) Appl. No.: 11/172,885

(22) Filed: Jul. 5, 2005

(65) Prior Publication Data

US 2006/0002872 A1    Jan. 5, 2006

Related U.S. Application Data

(60) Provisional application No. 60/589,007, filed on Jul. 20, 2004.

(30) Foreign Application Priority Data

Jul. 2, 2004 (FR) ..................................... 04 51421

(51) Int. Cl.
*A61Q 17/04* (2006.01)
*A61K 8/37* (2006.01)
*A61K 8/44* (2006.01)
*A61K 8/49* (2006.01)

(52) U.S. Cl.
CPC ................ *A61Q 17/04* (2013.01); *A61K 8/37* (2013.01); *A61K 8/44* (2013.01); *A61K 8/4966* (2013.01)

(58) Field of Classification Search
USPC ..................................... 424/59, 60, 400, 401
See application file for complete search history.

(56) References Cited

U.S. PATENT DOCUMENTS

| | | | |
|---|---|---|---|
| 5,882,633 A | 3/1999 | Pisson et al. | |
| 6,033,648 A * | 3/2000 | Candau | 424/59 |
| 6,355,264 B1 | 3/2002 | Garrison et al. | |
| 6,509,008 B1 * | 1/2003 | Candau | 424/59 |
| 7,132,097 B2 * | 11/2006 | Bertz et al. | 424/59 |
| 7,166,275 B2 | 1/2007 | Bertz et al. | |
| 2002/0197292 A1 * | 12/2002 | Fowler | 424/401 |
| 2005/0019280 A1 * | 1/2005 | Bertz et al. | 424/59 |
| 2005/0152858 A1 | 7/2005 | Bertz et al. | |
| 2005/0281763 A1 | 12/2005 | Suginaka et al. | |
| 2005/0288205 A1 | 12/2005 | Walele et al. | |
| 2006/0067900 A1 | 3/2006 | Bertz et al. | |
| 2006/0067901 A1 | 3/2006 | Bertz et al. | |

FOREIGN PATENT DOCUMENTS

| | | |
|---|---|---|
| AU | B-60074/96 | 1/1997 |
| AU | 2002-48839 A1 | 1/2003 |
| EP | 0 748 623 A1 | 12/1996 |
| EP | 1 269 980 A1 | 1/2003 |
| FR | 2757056 A1 | 6/1998 |
| FR | 2826264 A1 | 2/2002 |
| JP | 10-175837 A | 6/1998 |
| JP | 3043427 A | 3/2000 |
| JP | 2002-226350 A | 8/2002 |
| JP | 2003-26559 A | 1/2003 |
| WO | WO 97/00066 A1 | 1/1997 |
| WO | WO 03/039510 A1 | 5/2003 |
| WO | WO 2005/009341 A2 | 2/2005 |
| WO | WO 2005/069822 A2 | 8/2005 |
| WO | 2005/117823 A1 | 12/2005 |
| WO | 2005/117824 A1 | 12/2005 |
| WO | 2006/009828 A1 | 1/2006 |
| WO | WO 2006/000928 A2 | 1/2006 |
| WO | WO 2006/041506 A2 | 4/2006 |

OTHER PUBLICATIONS

Office Action ("Official Inquiry and Summary of Official Inquiry") dated Jun. 8, 2010, issued by the Japanese Patent Office in corresponding Japanese Patent Application No. 2005-194386.
Japanese Official Action dated Feb. 27, 2007 comments and Notice of Reasons for Rejection.
French Search Report corresponding to FR 04/51421, issued on Feb. 18, 2005, 1 page.

* cited by examiner

*Primary Examiner* — John Pak
*Assistant Examiner* — Luke Karpinski
(74) *Attorney, Agent, or Firm* — Buchanan Ingersoll & Rooney PC

(57) ABSTRACT

Topically applicable photoprotective compositions having improved sun protection factor, cosmetic properties and/or stability contain:
(a) at least one 1,3,5-triazine UV-screening agent,
(b) at least one mixture including:
  (i) at least one arylalkyl benzoate compound, and
  (ii) at least one oil containing in its structure at least one amide unit.

22 Claims, No Drawings

SOLUBILIZATION OF TRIAZINE UV-SCREENING AGENTS WITH ARYLALKYL BENZOATE COMPOUNDS/AMIDE-BASED OILS AND PHOTOPROTECTIVE COMPOSITIONS COMPRISED THEREOF

CROSS-REFERENCE TO PRIORITY/PROVISIONAL APPLICATIONS

This application claims priority under 35 U.S.C. §119 of FR 04/51421, filed Jul. 2, 2004, and of provisional application Ser. No. 60/589,007, filed Jul. 20, 2004, each hereby expressly incorporated by reference and each assigned to the assignee hereof. This application is also a continuation of said '007 provisional.

BACKGROUND OF THE INVENTION

Technical Field of the Invention:

The present invention relates to photoprotective compositions comprising at least one 1,3,5-triazine compound dissolved within a mixture of at least one arylalkyl benzoate compound and at least one amide-based oil, and also to various cosmetic applications thereof, especially for protecting the skin and/or the lips and/or the integuments against the deleterious effects of ultraviolet radiation, in particular solar radiation.

Description of Background and/or Related and/or Prior Art:

It is known that light radiation with wavelengths of from 280 nm to 400 nm permits tanning of the human epidermis, and that rays with wavelengths of from 280 nm to 320 nm, known as UV-B rays, cause skin burns and erythema which may be harmful to the development of a natural tan; this UV-B radiation should thus be screened out.

It is also known that UV-A rays, with wavelengths of from 320 nm to 400 nm, which cause tanning of the skin, are liable to induce an adverse change therein, especially in the case of sensitive skin or of skin which is continually exposed to solar radiation. UV-A rays cause in particular a loss of elasticity of the skin and the appearance of wrinkles, leading to premature skin aging. Same promote triggering of the erythemal reaction or amplify this reaction in certain individuals and may even be the cause of phototoxic or photoallergic reactions. It is thus desirable also to screen out UV-A radiation.

Many cosmetic compositions intended for the photoprotection (UV-A and/or UV-B) of the skin have been proposed to date.

These antisun compositions are quite often in the form of emulsion of oil-in-water type (that is to say, a cosmetically acceptable support comprising a continuous aqueous dispersing phase and a discontinuous oily dispersed phase) which contains, in various concentrations, one or more conventional lipophilic and/or hydrophilic organic screening agents which are capable of selectively absorbing harmful UV radiation, these screening agents (and their amounts) being selected as a function of the desired sun protection factor, the sun protection factor (SPF) being expressed mathematically by the ratio of the UV radiation dose necessary to reach the erythema-forming threshold with the UV screening agent to the UV radiation dose necessary to reach the erythema-forming threshold without UV screening agent.

1,3,5-Triazine derivatives are particularly desired in antisun cosmetics due to the fact that they are highly active in the UV-B range, and even in the UV-A range for some of these compounds, depending on the nature of the substituents involved. Furthermore, they are photostable, i.e., they show little or no chemical degradation under the action of UV radiation. They are especially described in U.S. Pat. No. 4,367,390, EP-863,145, EP-517,104, EP-570,838, EP-796,851, EP-775,698, EP-878,469 and EP-933,376, and the following are known, in particular:

2,4,6-tris[p-(2'-ethylhexyl-1'-oxycarbonyl)anilino]-1,3,5-triazine or "Ethylhexyl Triazone" (INCI name), marketed under the trademark "Uvinul T 150" by BASF, 2-[(p-(tert-butylamido)anilino]-4,6-bis-[(p-(2'-ethylhexyl-1'-oxycarbonyl)anilino]-1,3,5-triazine or "Diethylhexyl Butamido Triazone" (INCI name), marketed under the trademark "Uvasorb HEB" by Sigma 3V, 2,4-bis{[4-2-ethylhexyloxy)]-2-hydroxy]phenyl}-6-(4-methoxyphenyl)-1,3,5-triazine or "Bis-Ethylhexyloxyphenol Methoxyphenyl Triazine" (INCI name), marketed under the trademark "Tinosorb S" by Ciba Specialty Chemicals.

It has heretofore been proposed to include 1,3,5-triazine derivatives in oils such as esters and more particularly $C_{12}$-$C_{15}$ alkyl benzoates ("Finsolv TN" from Finetex), or triglycerides and especially $C_8$-$C_{12}$ fatty acid triglycerides ("Miglyol 812" from Hüls), or, alternatively, oxyethylenated or oxypropylenated fatty monoalcohols or polyols ("Cetiol HE" from Henkel or "Witconol AM" from Witco). The use of these oils presents two drawbacks:

(i) either the appearance over time of crystallization in the formulations, which is detrimental to the cosmetic qualities, the stability and the efficacy of antisun products; or (ii) the limitation of the concentration of screening agents in the formulations, which does not make it possible to obtain products that are sufficiently effective.

The technical problem underlying the present invention is thus that of improving the photoprotective efficacy, the cosmetic properties and the stability of compositions containing such 1,3,5-triazine derivatives.

With this objective, it has already been proposed in EP-0-748,623 to add to 2,4,6-tris[p-(2'-ethylhexyl-1'-oxycarbonyl)anilino]-1,3,5-triazine or "Ethylhexyl Triazone" N,N-disubstituted amide-based compounds without emulsifying properties, for instance N,N-diethyl-3-methylbenzamide or ethyl N-butyl-N-acetylaminopropionate.

It has also been proposed in EP-1-269,980 to add to UV-screening agents of triazine type N-acyl esters of amino acids, for instance isopropyl N-lauroylsarcosinate.

The results obtained with these amide-based oils are still not entirely satisfactory.

SUMMARY OF THE INVENTION

It has now surprisingly and unexpectedly been discovered that the disadvantages and drawbacks indicated above can be avoided or ameliorated by using a mixture of amide-based oil and of arylalkyl benzoate compound in a composition containing at least one triazine sunscreen, in an amount that is sufficient for dissolving by itself all of the triazine compound.

This particular mixture makes it possible to produce stable antisun/sunscreen compositions containing 1,3,5-triazine compounds, which have a sun protection factor higher than those of the prior art compositions containing 1,3,5-triazine derivatives and amide-based oils. These compositions also have improved cosmetic qualities. They especially allow good moisturization of the skin, i.e., no dryness of the skin and no greasy feel are observed.

The present invention thus features photoprotective cosmetic or dermatological compositions containing:

a) at least one 1,3,5-triazine UV-photoprotecting compound, and b) at least one mixture of at least one oil containing in its structure at least one amide structural unit and at least one arylalkyl benzoate compound.

This invention also features the formulation of such a composition for the manufacture of cosmetic or dermatological compositions suited, in particular, for protecting keratin materials against solar radiation.

The present invention also features incorporating a mixture of at least one oil containing in its structure at least one amide unit and at least one arylalkyl benzoate compound in a photoprotective cosmetic or dermatological composition containing at least one 1,3,5-triazine compound, in order to improve the sun protection factor and/or the cosmetic qualities and/or the stability of this composition.

Other aspects of the invention will become apparent from the description and the examples that follow.

DETAILED DESCRIPTION OF BEST MODE AND SPECIFIC/PREFERRED EMBODIMENTS OF THE INVENTION

The expression "photoprotective composition" means any composition containing at least one organic compound and/or at least one mineral compound capable of screening out UV-A and/or UV-B radiation via a phenomenon of absorption, reflection or scattering.

The expression "oil containing in its structure at least one amide unit" will be understood throughout this text to mean any compound comprising in its chemical structure at least one amide group (or function) of the type:

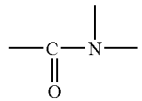

and simultaneously having the following characteristics:
a) liquid at 25° C.,
b) insoluble or immiscible in water at 25° C.,
c) no emulsifying properties.

Preferably, the amide-based oil/arylalkyl benzoate compound mixture is present in the composition in a sufficient amount to make it possible by itself to dissolve (without it being necessary to use another solvent) the total amount of triazine screening agent present in the composition.

The oil(s) having in their structure at least one amide unit in accordance with the invention is (are) preferably selected from the compounds of formula (1) below:

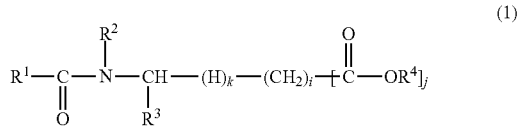

in which:
the radical $R^1$ is an optionally functionalized, aliphatic, cycloaliphatic or cyclic, saturated or unsaturated monovalent hydrocarbon-based radical having from 1 to 30 carbon atoms and preferably from 1 to 22 carbon atoms, inclusive;

the radicals $R^2$, $R^3$ and $R^4$, which may be identical or different, are each optionally functionalized, aliphatic, cycloaliphatic or cyclic, saturated or unsaturated monovalent hydrocarbon-based radicals having from 1 to 30 carbon atoms and preferably from 1 to 22 carbon atoms, inclusive;

k is 0 or 1;
i is an integer ranging from 0 to 2;
j is 0 or 1;
with the proviso that when j=1, then k is 0 and when j=0, then i=0 and k=1.

Examples of saturated aliphatic hydrocarbon-based radicals that are especially representative are linear or branched, substituted or unsubstituted $C_1$-$C_{30}$ and preferably $C_1$-$C_{22}$ alkyl radicals, and in particular methyl, ethyl, n-propyl, isopropyl, n-butyl, isobutyl, tert-butyl, pentyl, n-amyl, isoamyl, neopentyl, n-hexyl, n-heptyl, n-octyl, 2-ethylhexyl, tert-octyl, decyl, lauryl and octadecyl radicals.

Examples of saturated cyclic hydrocarbon-based radicals that are especially representative are cyclopentyl and cyclohexyl radicals, which are optionally substituted, in particular with alkyl radicals.

Examples of unsaturated aliphatic hydrocarbon-based radicals that are especially representative are linear or branched, substituted or unsubstituted, $C_2$-$C_{30}$ and preferably $C_2$-$C_{22}$ alkenyl or alkynyl radicals, and in particular vinyl, allyl, oleyl and linoleyl radicals.

Examples of unsaturated cyclic hydrocarbon-based radicals that are especially representative are aryl radicals such as phenyl and naphthyl, which are optionally substituted, in particular with alkyls, for instance a tolyl radical, and examples of unsaturated cycloaliphatic radicals that may be mentioned more particularly include benzyl and phenylethyl radicals.

The term "functionalized radicals" more particularly means radicals comprising in their chemical structure, either in the main chain or on a secondary chain unit, one or more functional groups especially such as esters, ethers, alcohols, amines, amides and ketones, but preferably esters.

The preferred amide-based oils of formula (1) are selected from those in which:

$R^1$ is a linear or branched $C_1$-$C_{22}$ alkyl radical, a linear or branched $C_2$-$C_{22}$ alkenyl radical, or an aryl radical;

$R^2$ is a hydrogen atom or a linear or branched $C_1$-$C_6$ alkyl radical;

$R^3$ is a hydrogen atom or a linear or branched $C_1$-$C_6$ alkyl radical; and $R^4$ is a linear or branched $C_1$-$C_{10}$ alkyl radical or a linear or branched $C_2$-$C_{10}$ alkenyl radical or a sterol residue.

In formula (1) presented above, the group $R^1(CO)$— is an acyl group of an acid preferably selected from the group consisting of acetic acid, toluic acid, capric acid, lauric acid, myristic acid, palmitic acid, stearic acid, behenic acid, linoleic acid, linolenic acid, oleic acid, isostearic acid, 2-ethylhexanoic acid, coconut oil fatty acids and palm kernel oil fatty acids. These acids may also contain a hydroxyl group.

In formula (1), when j is 1, the moiety —N($R^2$)CH($R^3$)(CH$_2$)q(CO)— of the amino acid ester is preferably selected from those corresponding to the following amino acids:

glycine, alanine, valine, leucine, isoleucine, serine, threonine, proline, hydroxyproline, β-alanine, N-butyl-β-alanine, aminobutyric acid, aminocaproic acid, sarcosine or N-methyl-β-alanine.

In formula (1), when j is 1, the moiety of the amino acid esters corresponding to the group $OR^4$ may be obtained from alcohols selected from the group consisting of methanol, ethanol, isopropanol, butanol, tert-butanol, isobutanol, 3-methyl-1-butanol, 2-methyl-1-butanol, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol and isostearyl alcohol.

The oils containing in their structure at least one amide function of formula (1) in accordance with the invention are known per se. Certain of these are especially described with their methods of preparation in EP-1-044,676 and EP-0-928,608 from the company Ajinomoto Co. Others are known in cosmetics, for instance insect repellents such as ethyl N-acetyl-N-butylaminopropionate or N,N-diethyltoluamide.

Among the compounds of formula (1) that are particularly preferred, mention may be made of:

ethyl N-acetyl-N-butylaminopropionate, having the following formula:

$$H_3C-\underset{\underset{O}{\|}}{C}-\underset{\underset{(CH_2)_3CH_3}{|}}{N}-(CH_2)_2-\underset{\underset{O}{\|}}{C}-OCH_2CH_3$$

such as the product marketed under the trademark Repellent R3535 by Merck;

isopropyl N-lauroylsarcosinate of formula:

$$H_3C-(CH_2)_{11}-\underset{\underset{O}{\|}}{C}-\underset{\underset{CH_3}{|}}{N}-CH_2-\underset{\underset{O}{\|}}{C}-O-CH\underset{CH_3}{\overset{CH_3}{<}}$$

such as the product marketed under the name Eldew SL-205 by Ajimoto;

N,N-diethyltoluamide of formula:

[structure of N,N-diethyltoluamide]

such as the product marketed under the trademark Deet by Showa Denko.

The oil(s) containing in their structure at least one amide function as defined above is (are) present in the compositions according to the invention in concentrations preferably ranging from 0.1% to 40% by weight and more preferably from 1% to 20% by weight relative to the total weight of the composition.

The arylalkyl benzoate compounds in accordance with the invention are preferably selected from those of formula (2) or (3) below:

$$R^5-\text{[benzoyl]}-X-(CH_2)_n-\text{[phenyl]}-R^6 \quad (2)$$

$$(3)$$

[structure of formula (3) with R7, R8, R9 substituents]

in which:
X is O, S or N;
n is an integer ranging from 1 to 10 and more preferably from 2 to 6;
$R^5$ and $R^6$, which may be identical or different, are each a hydrogen atom, a hydroxyl group, a linear or branched $C_1$-$C_4$ alkoxy radical (preferably methoxy or ethoxy), a nitro radical, an amino radical, or a $C_6H_6SO_2$ radical;
$R^7$, $R^8$ and $R^9$, which may be identical or different, are each a radical of formula:

$$-(CH_2)_n-\text{[phenyl]}-R^{10}$$

in which n has the same definition as indicated above; and $R^{10}$ is a hydrogen atom, a hydroxyl group, a linear or branched $C_1$-$C_4$ alkoxy radical (preferably methoxy or ethoxy), a nitro radical, an amino radical, or a $C_6H_6SO_2$ radical.

The arylalkyl benzoate compounds in accordance with the invention and the syntheses thereof have long been known in the chemical literature and especially in PL-55230.

Among the arylalkyl benzoate compounds mentioned above, 2-phenylethyl benzoate of formula:

[structure of 2-phenylethyl benzoate]

for instance the commercial product X-Tend 226® marketed by ISP will be used more particularly.

The arylalkyl benzoate compounds in accordance with the invention may be present in the compositions in accordance with the invention in contents ranging from 0.1% to 40% by weight and more preferably from 1% to 30% by weight relative to the total weight of the composition.

The 1,3,5-triazine derivative corresponds to formula (I) below:

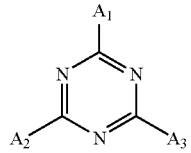
(I)

in which the radicals $A_1$, $A_2$ and $A_3$, which may be identical or different, are selected from the groups of formulae (II) to (IX) below:

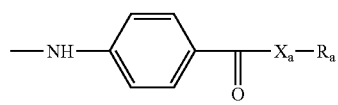
(II)

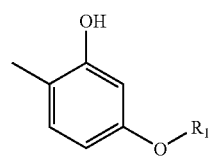
(III)

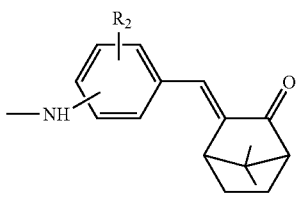
(IV)

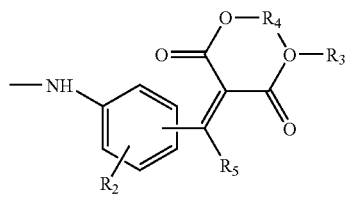
(V)

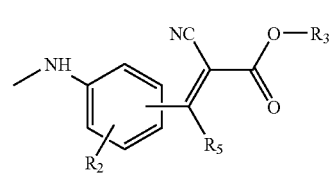
(VI)

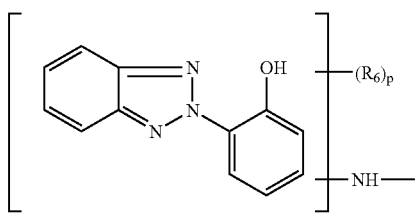
(VII)

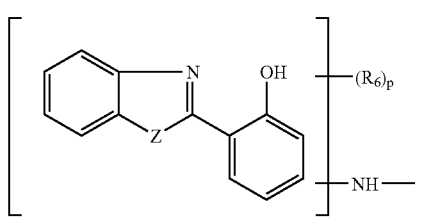
(VIII)

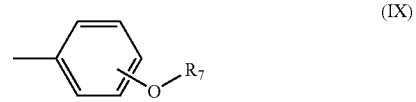
(IX)

in which:

$X_a$ (each of the groups $X_a$ may be identical or different) is oxygen or —NH—;

$R_a$ (each of the groups $R_a$ may be identical or different) is selected from hydrogen, an alkali metal, an ammonium radical optionally substituted with one or more linear or branched $C_1$-$C_{18}$ alkyl or linear or branched $C_1$-$C_{18}$ hydroxyalkyl radicals, a linear or branched $C_1$-$C_{18}$ and preferably $C_6$-$C_{12}$ alkyl radical, a $C_5$-$C_{12}$ cycloalkyl radical optionally substituted with one or more $C_1$-$C_4$ alkyl radicals, a polyoxyethylenated radical comprising from 1 to 6 ethylene oxide units, the terminal OH group of which is methylated, a radical of formula (X), (XI) or (XII) below:

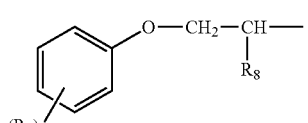
(X)

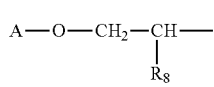
(XI)

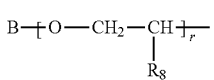
(XII)

in which:

$R_8$ is hydrogen or a methyl radical;
$R_9$ is a $C_1$-$C_9$ alkyl radical;
q is an integer equal to 0; 1; 2; 3;
r is an integer equal to 1; 2; 3; 4; 5; 6; 7; 8; 9; 10;
A is a $C_4$-$C_8$ alkyl radical or a $C_5$-$C_8$ cycloalkyl radical;
B is selected from among a linear or branched $C_1$-$C_8$ alkyl radical, a $C_5$-$C_8$ cycloalkyl radical, an aryl radical optionally substituted with one or more $C_1$-$C_4$ alkyl radicals;
$R_1$ is a $C_3$-$C_{18}$ alkyl radical, a $C_2$-$C_{18}$ alkenyl radical, a residue of formula —CH$_2$—CH(OH)—CH$_2$—OT$_1$ in which $T_1$ is a hydrogen atom or a $C_1$-$C_8$ alkyl radical, a residue of formula (XIII) below:

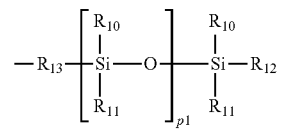
(XIII)

in which:

$R_{13}$ is a covalent bond, a linear or branched $C_1$-$C_4$ alkyl radical or a radical of formula —$C_{m1}H_{2m1}$—O— in which $m_1$ is an integer equal to 1; 2; 3; 4;

$p_1$ is an integer equal to 0; 1; 2; 3; 4; 5;

the radicals $R_{10}$, $R_{11}$ and $R_{12}$, which may be identical or different, are each a $C_1$-$C_{18}$ alkyl radical, a $C_1$-$C_{18}$ alkoxy radical or a radical of formula:

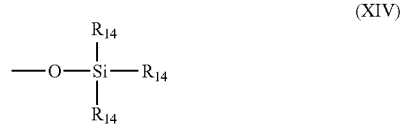

(XIV)

in which $R_{14}$ is a $C_1$-$C_5$ alkyl radical;

$R_2$ is a hydrogen atom, a linear or branched $C_1$-$C_4$ alkyl radical or a $C_1$-$C_4$ alkoxy radical;

$R_3$ and $R_4$, which may be identical or different, are each a linear or branched $C_1$-$C_{20}$ alkyl radical;

$R_5$ is a hydrogen atom or a phenyl radical optionally substituted with a halogen or with a $C_1$-$C_4$ alkyl radical or with a $C_1$-$C_4$ alkoxy radical;

$R_6$ is a linear or branched $C_1$-$C_8$ alkyl radical or a $C_1$-$C_3$ alkoxy radical, it being understood that, in the latter case, two adjacent radicals $R_6$ on the same aromatic nucleus can together form an alkylidenedioxy group in which the alkylidene group contains 1 or 2 carbon atoms, OH, NHCOCH$_3$ or NH$_2$;

$R_7$ is a hydrogen atom, a $C_1$-$C_{10}$ alkyl radical, a radical of formula: —(CH$_2$CHR$_5$—O)$_{n1}$R$_8$ in which $n_1$ is a number ranging from 1 to 16, or a radical of structure —CH$_2$—CH—(OH)—CH$_2$OT$_1$ with $R_8$ and $T_1$ having the same definition as indicated above, Z is oxygen, sulfur, —NH— or —NR$_3$— with $R_3$ representing a linear or branched $C_1$-$C_{20}$ alkyl radical;

p is 0, 1, 2 or 3;

$A_1$ can also be a halogen, a radical —N(R$_3$)$_2$, the two radicals $R_3$ together optionally forming a ring of 4 or 5 carbon atoms, or a group —OR$_3$, $R_3$ having the same definition as above.

A first family of 1,3,5-triazine derivatives that is more particularly preferred, and that is described especially in EP-A-0-517,104, is that of the 1,3,5-triazines corresponding to formula (I) in which $A_1$, $A_2$ and $A_3$ are of formula (II) and have all of the following characteristics:

one of the groups $X_a$-$R_a$ is a radical —NH—$R_a$ with $R_a$ selected from among a $C_5$-$C_{12}$ cycloalkyl radical optionally substituted with one or more $C_1$-$C_4$ alkyl radicals, a radical of formula (X), (XI) or (XII) above in which:

B is a $C_1$-$C_4$ alkyl radical;

$R_9$ is a methyl radical;

the other two groups $X_a$-$R_a$ is a radical —O—$R_a$ with $R_a$, which may be identical or different, selected from among hydrogen, an alkali metal, an ammonium radical optionally substituted with one or more alkyl or hydroxyalkyl radicals, a linear or branched $C_1$-$C_{18}$ alkyl radical, a $C_5$-$C_{12}$ cycloalkyl radical optionally substituted with one or more $C_1$-$C_4$ alkyl radicals, a radical of formula (X), (XI) or (XII) above, in which:

B is a $C_1$-$C_4$ alkyl radical;

$R_9$ is a methyl radical.

A second family of 1,3,5-triazine derivatives that is more particularly preferred, and that is described especially in EP-A-0-570,838, is that of the 1,3,5-triazines corresponding to formula (I) in which $A_1$, $A_2$ and $A_3$ are of formula (II) and have all of the following characteristics:

one or two groups $X_a$-$R_a$ is a radical —NH—$R_a$, with $R_a$ selected from among a linear or branched $C_1$-$C_{18}$ alkyl radical, a $C_5$-$C_{12}$ cycloalkyl radical optionally substituted with one or more $C_1$-$C_4$ alkyl radicals, a radical of formula (X), (XI) or (XII) above in which B is a $C_1$-$C_4$ alkyl radical and $R_9$ is a methyl radical;

the other or the other two group(s) $X_a$-$R_a$ being a radical —O—$R_a$ with $R_a$, which may be identical or different, selected from among hydrogen, an alkali metal, an ammonium radical optionally substituted with one or more alkyl or hydroxyalkyl radicals, a linear or branched $C_1$-$C_{18}$ alkyl radical, a $C_5$-$C_{12}$ cycloalkyl radical optionally substituted with one or more $C_1$-$C_4$ alkyl radicals, a radical of formula (X), (XI) or (XII) above in which B is a $C_1$-$C_4$ alkyl radical and $R_9$ is a methyl radical.

A 1,3,5-triazine of this second family that is particularly preferred is 2-[(p-(tert-butylamido)anilino]-4,6-bis[(p-(2'-ethylhexyl-1'-oxycarbonyl)anilino]-1,3,5-triazine or "Diethylhexyl Butamido Triazone" marketed under the trademark "Uvasorb HEB" by Sigma 3V and corresponding to the following formula:

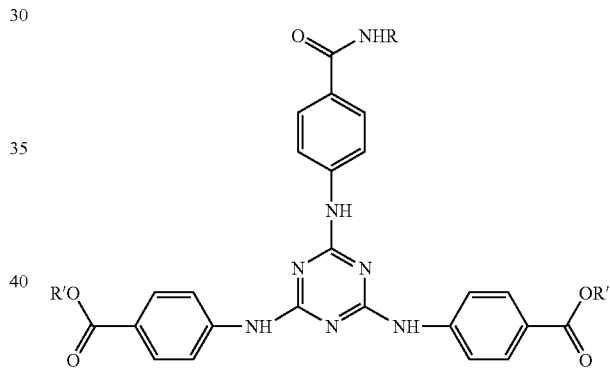

in which R' is a 2-ethylhexyl radical and R is a tert-butyl radical.

A third preferred family of compounds that may be used in the context of the present invention, and which is described especially in U.S. Pat. No. 4,724,137, is that of the 1,3,5-triazines corresponding to formula (I) in which $A_1$, $A_2$ and $A_3$ are of formula (II) and have all of the following characteristics:

$X_a$ are identical and represent oxygen;

$R_a$, which may be identical or different, is a $C_6$-$C_{12}$ alkyl radical or a polyoxyethylenated radical comprising from 1 to 6 ethylene oxide units, the terminal OH group of which is methylated.

A 1,3,5-triazine of this third family that is particularly preferred is 2,4,6-tris[p(2'-ethylhexyl-1'-oxycarbonyl)anilino]-1,3,5-triazine or "Ethylhexyl Triazone" marketed especially under the trademark "Uvinul T 150" by BASF and corresponds to the following formula:

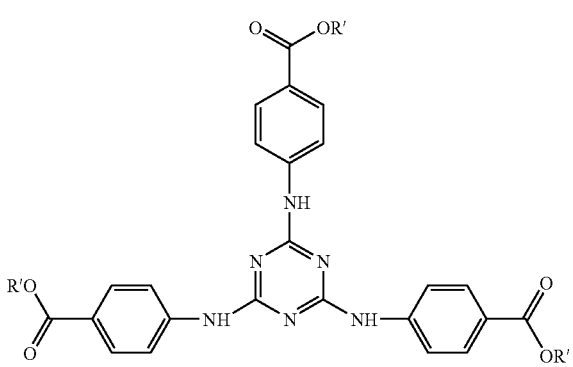

in which R' is a 2-ethylhexyl radical.

A fourth preferred family of compounds that may be used in the context of the present invention, and which is described especially in EP-A-0-775,698, is that of the 1,3,5-triazines corresponding to formula (I) in which $A_1$ and $A_2$ are of formula (III) and $A_3$ is of formula (IX) and have all of the following characteristics: $R_1$, which may be identical or different, are each a $C_3$-$C_{18}$ alkyl radical, a $C_2$-$C_{18}$ alkenyl radical or a residue of formula —$CH_2$—$CH(OH)$—$CH_2$—$OT_1$ in which $T_1$ is a hydrogen atom or a $C_1$-$C_8$ alkyl radical, $R_7$ is a hydrogen atom or a $C_1$-$C_{10}$ alkyl radical.

A 1,3,5-triazine of this fourth family that is particularly preferred is 2,4-bis{[4-2-ethylhexyloxy)]-2-hydroxy]phenyl}-6-(4-methoxyphenyl)-1,3,5-triazine or "Anisotriazine" marketed under the trademark "Tinosorb S" by Ciba Specialty Chemicals, and corresponds to the following formula:

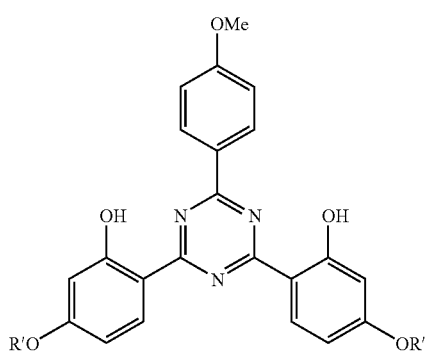

in which R' is a 2-ethylhexyl radical.

A fifth preferred family of compounds that may be used in the context of the present invention, and which is described especially in EP-507,691, EP-507,692, EP-790,243 and EP-944,624, and the technical content of which is incorporated in its entirety in the present description, is that of the 1,3,5-triazines corresponding to formula (I) in which $A_1$, $A_2$ and $A_3$ are of formulae (VII) to (XI) mentioned above.

As examples of these compounds that may be used, representative are:
2,4,6-tris(diisobutyl 4'-aminobenzalmalonate)-s-triazine,
2,4,6-tris(bis(2-ethylhexyl)4'-aminobenzalmalonate)-s-triazine,
2,4,6-tris(bis(2-ethylhexyl)4'-aminobenzalmalonate)-6-chloro-s-triazine,
2,4,6-tris(bis(2-ethylhexyl)4'-aminobenzalmalonate)-6-(2-ethylhexyl 4'-aminobenzoate)-s-triazine,
2,4,6-tris(diisobutyl 4'-aminobenzalmalonate)-6-butoxy-s-triazine,
2,4,6-tris(diisobutyl 4'-aminobenzalmalonate)-6-(2-ethylhexylamino)-s-triazine,
2,4-bis(4'-aminobenzylidenecamphor)-6-(2-ethylhexylamino)-s-triazine,
2,4-bis(4'-aminobenzylidenecamphor)-6-(diisobutyl 4'-aminobenzalmalonate)-s-triazine,
2,4,6-tris(diethyl 4'-aminobenzalmalonate)-s-triazine,
2,4,6-tris(diisopropyl 4'-aminobenzalmalonate)-s-triazine,
2,4,6-tris(dimethyl 4'-aminobenzalmalonate)-s-triazine,
2,4,6-tris(ethyl α-cyano 4-aminocinnamate)-s-triazine,
2,4,6-tris[(3'-benzotriazol-2-yl-2'-hydroxy-5'-methyl)phenylamino]-s-triazine,
2,4,6-tris[(3'-benzotriazol-2-yl-2'-hydroxy-5'-tert-octyl)phenylamino]-s-triazine.

A 1,3,5-triazine of this fifth family that is particularly preferred is 2,4,6-tris(diisobutyl 4'-aminobenzalmalonate)-s-triazine, which corresponds to the following formula:

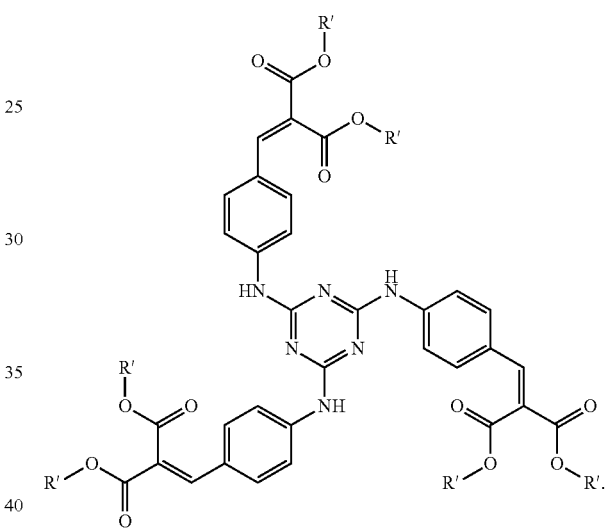

The compositions according to the present invention preferably comprise, in a physiologically acceptable medium, from 0.05% to 15% and preferably from 0.1% to 10% of 1,3,5-triazine derivatives by weight relative to the total weight of the said composition.

The said compositions according to the present invention are preferably cosmetic compositions containing, besides the 1,3,5-triazine derivative as organic screening agent, at least one other additional organic screening agent and/or at least one other additional mineral screening agent, which is water-soluble, liposoluble or insoluble in the cosmetic solvents commonly used.

The compositions in accordance with the invention may also comprise other additional UV-A-active and/or UV-B-active organic or mineral photoprotective agents that are water-soluble or liposoluble or insoluble in the cosmetic solvents commonly used.

The additional organic photoprotective agents are selected especially from anthranilates; cinnamic derivatives; salicylic derivatives; camphor derivatives; benzophenone derivatives; β,β-diphenylacrylate derivatives; benzotriazole derivatives; benzalmalonate derivatives; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2-303,549, DE-197,26, 184 and EP-893,119; benzoxazole derivatives as described in EP-0-832,642, EP-1-027,883, EP-1-300,137 and DE-101, 62,844; screening polymers and screening silicones such as those described especially in patent application WO 93/04665; dimers derived from α-alkylstyrene, such as those described in DE-198,55,649; 4,4-diarylbutadienes such as those described in EP-0-967,200, DE-197,46,654, DE-197, 55,649, EP-A-1-008,586, EP-1-133,980 and EP-133,981, and mixtures thereof.

As examples of additional organic screening agents, representative are those denoted hereinbelow under their INCI name:

Para-Aminobenzoic Acid Derivatives:
PABA,
Ethyl PABA,
Ethyl dihydroxypropyl PABA,
Ethylhexyl dimethyl PABA marketed in particular under the name "Escalol 507" by ISP,
Glyceryl PABA,
PEG-25 PABA marketed under the name "Uvinul P25" by BASF.
Salicylic Derivatives:
Homosalate marketed under the name "Eusolex HMS" by Rona/EM Industries,
Ethylhexyl salicylate marketed under the name "Neo Heliopan OS" by Haarmann and Reimer,
Dipropylene glycol salicylate marketed under the name "Dipsal" by Scher,
TEA salicylate marketed under the name "Neo Heliopan TS" by Haarmann and Reimer.
Cinnamic Derivatives:
Ethylhexyl methoxycinnamate marketed in particular under the trademark "Parsol MCX" by Hoffmann LaRoche,
Isopropyl methoxycinnamate,
Isoamyl methoxycinnamate marketed under the trademark "Neo Heliopan E 1000" by Haarmann and Reimer,
Cinoxate,
DEA methoxycinnamate,
Diisopropyl methylcinnamate,
Glyceryl ethylhexanoate dimethoxycinnamate.
β,β-Diphenylacrylate Derivatives:
Octocrylene marketed in particular under the trademark "Uvinul N539" by BASF,
Etocrylene marketed in particular under the trademark "Uvinul N35" by BASF.
Benzophenone Derivatives:
Benzophenone-1 marketed under the trademark "Uvinul 400" by BASF,
Benzophenone-2 marketed under the trademark "Uvinul D50" by BASF,
Benzophenone-3 or Oxybenzone marketed under the trademark "Uvinul M40" by BASF,
Benzophenone-4 marketed under the trademark "Uvinul MS40" by BASF,
Benzophenone-5,
Benzophenone-6 marketed under the trademark "Helisorb 11" by Norquay,
Benzophenone-8 marketed under the trademark "Spectra-Sorb UV-24" by American Cyanamid,
Benzophenone-9 marketed under the trademark "Uvinul DS-49" by BASF,
Benzophenone-12,
n-Hexyl 2-(4-diethylamino-2-hydroxybenzoyl)benzoate.

Benzylidenecamphor Derivatives:
3-Benzylidenecamphor manufactured under the name "Mexoryl SD" by Chimex,
4-Methylbenzylidenecamphor marketed under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.
Phenylbenzimidazole Derivatives:
Phenylbenzimidazolesulfonic acid marketed in particular under the trademark "Eusolex 232" by Merck,
Disodium phenyldibenzimidazoletetrasulfonate marketed under the trademark "Neo Heliopan AP" by Haarmann and Reimer.
Phenylbenzotriazole Derivatives:
Drometrizole trisiloxane marketed under the name "Silatrizole" by Rhodia Chimie,
Methylenebis(benzotriazolyl)tetramethylbutylphenol marketed in solid form under the trademark "MIXXIM BB/100" by Fairmount Chemical, or in micronized form as an aqueous dispersion under the trademark "Tinosorb M" by Ciba Specialty Chemicals.
Anthranilic Derivatives:
Menthyl anthranilate marketed under the trademark "Neo Heliopan MA" by Haarmann and Reimer.
Imidazoline Derivatives:
Ethylhexyldimethoxybenzylidenedioxoimidazoline propionate.
Benzalmalonate Derivatives:
Polyorganosiloxane containing benzalmalonate functions, for instance Polysilicone-15, marketed under the trademark "Parsol SLX" by Hoffmann LaRoche
4,4-Diarylbutadiene Derivatives:
1,1-Dicarboxy(2,2'-dimethylpropyl)-4,4-diphenylbutadiene,
Benzoxazole Derivatives:
2,4-bis[5-1(dimethylpropyl)benzoxazol-2-yl(4-phenyl) imino]-6-(2-ethylhexyl)imino-1,3,5-triazine marketed under the name Uvasorb K2A by Sigma 3V,
and mixtures thereof.

The preferred additional organic UV-screening agents are selected from:
Homosalate,
Ethylhexyl salicylate,
Ethylhexyl methoxycinnamate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl) imino]-6-(2-ethylhexyl)imino-1,3,5-triazine,
and mixtures thereof.

The additional mineral photoprotective agents are selected from pigments and even more preferably nanopigments (mean size of the primary particles: generally from 5 nm to 100 nm and preferably from 10 nm to 50 nm) of treated or untreated metal oxides such as, for example, nanopigments of titanium oxide (amorphous or crystallized in rutile and/or anatase form), or of iron oxide, zinc oxide, zirconium oxide or cerium oxide.

The treated nanopigments are pigments that have undergone one or more surface treatments of chemical, electronic, mechanochemical and/or mechanical nature with compounds as described, for example, in *Cosmetics & Toiletries*, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen or elastin), alkanolamines, silicon oxides, metal oxides, sodium hexametaphosphate, alumina or glycerol.

The treated nanopigments may more particularly be titanium dioxides treated with:

silica and alumina, such as the products "Microtitanium Dioxide MT 500 SA" and "Microtitanium dioxide MT 100 SA" from the company Tayca, and the products "Tioveil Fin", "Tioveil OP", "Tioveil MOTG" and "Tioveil IPM" from the company Tioxide, alumina and aluminum stearate, such as the product "Microtitanium Dioxide MT 100 T" from the company Tayca, alumina and aluminum laurate, such as the product "Microtitanium Dioxide MT 100 S" from the company Tayca, iron oxides and iron stearate, such as the product "Microtitanium Dioxide MT 100 F" from the company Tayca, silica, alumina and silicone, such as the products "Microtitanium Dioxide MT 100 SAS", "Microtitanium Dioxide MT 600 SAS" and "Microtitanium Dioxide MT 500 SAS" from the company Tayca, sodium hexametaphosphate, such as the product "Microtitanium Dioxide MT 150 W" from the company Tayca, octyltrimethoxysilane, such as the product "T-805" from the company Degussa, alumina and stearic acid, such as the product "UVT-M160" from the company Kemira, alumina and glycerol, such as the product "UVT-M212" from the company Kemira, alumina and silicone, such as the product "UVT-M262" from the company Kemira.

Other titanium oxide nanopigments treated with a silicone are preferably $TiO_2$ treated with octyltrimethylsilane and for which the mean size of the elementary particles is from 25 to 40 nm, such as the product marketed under the trademark "T 805" by Degussa Silices, $TiO_2$ treated with a polydimethylsiloxane and for which the mean size of the elementary particles is 21 nm, such as the product marketed under the trademark "70250 Cardre UF TiO2Si3" by Cardre, anatase/rutile $TiO_2$ treated with a polydimethylhydrogenosiloxane and for which the mean size of the elementary particles is 25 nm, such as the product marketed under the trademark "Microtitanium Dioxide USP Grade Hydrophobic" by Colour Techniques.

The uncoated titanium oxide nanopigments are marketed, for example, by Tayca under the trademarks "Microtitanium Dioxide MT 500 B" or "Microtitanium Dioxide MT 600 B", by Degussa under the name "P 25", by Wackher under the name "Oxyde de titane transparent PW", by Miyoshi Kasei under the name "UFTR", by Tomen under the name "ITS" and by Tioxide under the name "Tioveil AQ".

The uncoated zinc oxide nanopigments are, for example: those marketed under the name "Z-Cote" by Sunsmart; those marketed under the name "Nanox" by Elementis; those marketed under the name "Nanogard WCD 2025" by Nanophase Technologies.

The coated zinc oxide nanopigments are, for example: those marketed under the name "Zinc Oxide CS-5" by Toshibi (ZnO coated with polymethylhydrogenosiloxane);

those marketed under the name "Nanogard Zinc Oxide FN" by Nanophase Technologies (as a 40% dispersion in Finsolv TN, $C_{12}$-$C_{15}$ alkyl benzoate);

those marketed under the name "Daitopersion ZN-30" and "Daitopersion ZN-50" by Daito (dispersions in cyclopolymethylsiloxane/oxyethylenated polydimethylsiloxane, containing 30% or 50% of nanozinc oxides coated with silica and polymethylhydrogenosiloxane);

those marketed under the name "NFD Ultrafine ZNO" by Daikin (ZnO coated with perfluoroalkyl phosphate and copolymer based on perfluoroalkylethyl as a dispersion in cyclopentasiloxane);

those marketed under the name "SPD-Z1" by Shin-Etsu (ZnO coated with silicone-grafted acrylic polymer, dispersed in cyclodimethylsiloxane);

those marketed under the name "Escalol Z100" by ISP (alumina-treated ZnO dispersed in an ethylhexyl methoxycinnamate/PVP-hexadecene copolymer/methicone mixture);

those marketed under the name "Fuji ZNO-SMS-10" by Fuji Pigment (ZnO coated with silica and polymethylsilsesquioxane);

those marketed under the name "Nanox Gel TN" by Elementis (ZnO dispersed at a concentration of 55% in $C_{12}$-$C_{15}$ alkyl benzoate with hydroxystearic acid polycondensate).

The uncoated cerium oxide nanopigments are marketed under the name "Colloidal Cerium Oxide" by Rhone-Poulenc.

The uncoated iron oxide nanopigments are marketed, for example, by Arnaud under the names "Nanogard WCD 2002 (FE 45B)" and "Nanogard Iron FE 45 BL AQ", "Nanogard FE 45R AQ", "Nanogard WCD 2006 (FE 45R)" or by Mitsubishi under the name "TY-220".

The coated iron oxide nanopigments are marketed, for example, by Arnaud under the names "Nanogard WCD 2008 (FE 45B FN)", "Nanogard WCD 2009 (FE 45B 556)", "Nanogard FE 45 BL 345", "Nanogard FE 45 BL" or by BASF under the name "Transparent Iron Oxide".

Mention may also be made of mixtures of metal oxides, especially of titanium dioxide and of cerium dioxide, including the silica-coated equal-weight mixture of titanium dioxide and of cerium dioxide, marketed by Ikeda under the name "Sunveil A", and also the alumina, silica and silicone-coated mixture of titanium dioxide and of zinc dioxide, such as the product "M 261" marketed by Kemira, or the alumina, silica and glycerol-coated mixture of titanium dioxide and of zinc dioxide, such as the product "M 211" marketed by Kemira.

The nanopigments may be introduced into the compositions according to the invention in unmodified form or in the form of pigmentary paste, i.e., as a mixture with a dispersant, as described, for example, in GB-A-2-206,339.

The additional photoprotective agents are generally present in the compositions according to the invention in proportions ranging from 0.01% to 20% by weight relative to the total weight of the composition and preferably ranging from 0.1% to 10% by weight relative to the total weight of the composition.

The compositions according to the invention may also contain agents for artificially tanning and/or browning the skin (self-tanning agents) and more particularly dihydroxyacetone (DHA). They are preferably present in amounts ranging from 0.1% to 10% by weight relative to the total weight of the composition.

The compositions in accordance with the present invention may also comprise standard cosmetic adjuvants selected especially from fatty substances, organic solvents, ionic or nonionic, hydrophilic or lipophilic thickeners, softeners, humectants, opacifiers, stabilizers, emollients, silicones, antifoams, fragrances, preservatives, anionic, cationic, nonionic, zwitterionic or amphoteric surfactants, active agents, fillers, polymers, propellants, acidifying or basifying agents or any other ingredient usually used in cosmetics and/or dermatology.

The fatty substances may consist of an oil or a wax or mixtures thereof. The term "oil" means a compound that is liquid at room temperature. The term "wax" means a compound that is solid or substantially solid at room temperature and whose melting point is generally greater than 35° C.

Oils that may be mentioned include mineral oils (paraffin); plant oils (sweet almond oil, macadamia oil, grapeseed oil or jojoba oil); synthetic oils, for instance perhydrosqualene, fatty alcohols, fatty acids or fatty esters (for instance the $C_{12}$-$C_{15}$ alkyl benzoate marketed under the trademark "Finsolv TN" by Witco, octyl palmitate, isopropyl lanolate and triglycerides, including capric/caprylic acid triglycerides), oxyethylenated or oxypropylenated fatty esters and ethers; silicone oils (cyclomethicone and polydimethylsiloxanes, or PDMS) or fluoro oils, and polyalkylenes.

Waxy compounds that may be mentioned include paraffin, carnauba wax, beeswax and hydrogenated castor oil.

Among the organic solvents that may be mentioned are lower alcohols and polyols. These polyols may be selected from glycols and glycol ethers, for instance ethylene glycol, propylene glycol, butylene glycol, dipropylene glycol or diethylene glycol.

Hydrophilic thickeners that may be mentioned include carboxyvinyl polymers such as the Carbopol products (carbomers) and the Pemulen products (acrylate/C10-C30-alkylacrylate copolymer); polyacrylamides, for instance the crosslinked copolymers marketed under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulfonic acid polymers and copolymers, which are optionally crosslinked and/or neutralized, for instance the poly(2-acrylamido-2-methylpropanesulfonic acid) marketed by Hoechst under the trademark "Hostacerin AMPS" (CTFA name: ammonium polyacryldimethyltauramide); cellulose-based derivatives such as hydroxyethylcellulose; polysaccharides and especially gums such as xanthan gum; and mixtures thereof.

Lipophilic thickeners that may be mentioned include modified clays such as hectorite and its derivatives, for instance the products marketed under the name Bentone.

Among the active agents that may be mentioned are:
antipollution agents and/or free-radical scavengers;
depigmenting agents and/or propigmenting agents;
antiglycation agents;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
desquamating agents;
moisturizers;
anti-inflammatory agents;
agents acting on the energy metabolism of cells;
insect repellants;
substance P or CGRP antagonists.

Needless to say, one skilled in this art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be prepared according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion, a powder or a solid stick, and may optionally be packaged as an aerosol and may be in the form of a mousse or a spray.

The compositions according to the invention are preferably in the form of an oil-in-water or water-in-oil emulsion.

The emulsions generally contain at least one emulsifier selected from amphoteric, anionic, cationic and nonionic emulsifiers, which are used alone or as a mixture. The emulsifiers are appropriately selected according to the emulsion to be obtained (W/O or O/W).

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, marketed under the name "DC 5225 C" by Dow Corning, and alkyldimethicone copolyols such as laurylmethicone copolyol marketed under the name "Dow Corning 5200 Formulation Aid" by Dow Corning; cetyldimethicone copolyol; such as the product marketed under the name Abil EM 90R by Goldschmidt, and the mixture of cetyldimethicone copolyol, of polyglyceryl isostearate (4 mol) and of hexyl laurate, marketed under the name Abil WE O9 by Goldschmidt. One or more co-emulsifiers may also be added thereto, which may be selected advantageously from the group comprising polyol alkyl esters. Polyol alkyl esters that may especially be mentioned include glycerol and/or sorbitan esters, for example polyglyceryl isostearate, such as the product marketed under the name Isolan GI 34 by Goldschmidt, sorbitan isostearate, such as the product marketed under the name Arlacel 987 by ICI, sorbitan glyceryl isostearate, such as the product marketed under the name Arlacel 986 by ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkyl ethers; sugar esters, for instance sucrose stearate; fatty alkyl ethers of sugars, especially alkylpolyglucosides (APG) such as decylglucoside and laurylglucoside marketed, for example, by Henkel under the respective names Plantaren 2000 and Plantaren 1200, cetostearyl glucoside optionally as a mixture with cetostearyl alcohol, marketed, for example, under the name Montanov 68 by SEPPIC, under the name Tegocare CG90 by Goldschmidt and under the name Emulgade KE3302 by Henkel, and also arachidyl glucoside, for example in the form of a mixture of arachidyl alcohol, behenyl alcohol and arachidyl glucoside, marketed under the name Montanov 202 by SEPPIC. According to one particular embodiment of the invention, the mixture of the alkylpolyglucoside as defined above with the corresponding fatty alcohol may be in the form of a self-emulsifying composition as described, for example, in WO-A-92/06778.

When it is an emulsion, the aqueous phase of this emulsion may comprise a nonionic vesicular dispersion prepared according to known processes (Bangham, Standish and Watkins, J. Mol. Biol., 13, 238 (1965), FR-2-315,991 and FR-2416,008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

The present invention also features the use of the subject compositions as defined above for the manufacture of products for cosmetically treating the skin, the lips, the nails, the hair, the eyelashes, the eyebrows and/or the scalp, especially care products and makeup products.

The cosmetic compositions according to the invention may be used, for example, as care products and/or antisun products for the face and/or the body, of liquid to semi-liquid consistency, such as milks, more or less rich creams, cream-gels and pastes. They may optionally be packaged as an aerosol and may be in the form of mousses or sprays.

The compositions according to the invention in the form of vaporizable fluid lotions are applied to the skin or the hair in the form of fine particles by means of pressurization devices. The devices in accordance with the invention are well known to those skilled in the art and include non-aerosol pumps or "atomizers", aerosol containers comprising a propellant and also aerosol pumps using compressed air as propellant. The latter pumps are described in U.S. Pat. Nos. 4,077,441 and 4,850,517 (forming an integral part of the content of the description).

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

| Composition | Example 1 | Example 2 |
|---|---|---|
| PHASE A: | | |
| Polydimethylsiloxane | 0.5 | 0.5 |
| Preservatives | 1.0 | 1.0 |
| Stearic acid | 1.5 | 1.5 |
| Glyceryl monostearate/PEG stearate mixture (100 EO) | 1.0 | 1.0 |
| Cetylstearyl glucoside/cetylstearyl alcohol mixture | 2.0 | 2.0 |
| Cetyl alcohol | 0.5 | 0.5 |
| Butylmethoxydibenzoylmethane | 2.0 | 2.0 |
| 2-phenylethyl benzoate (X-Tend 226 from ISP) | 10 | 10 |
| N-Lauroyl isopropyl sarcosinate (Eldew SL-205-Ajinomoto) | 10 | 10 |
| Bis(ethylhexyloxyphenol)methoxyphenyltriazine (Tinosorb S from Ciba Geigy) | 5 | — |
| Ethylhexyl Triazone (Uvinul T150 from BASF) | — | 5 |
| PHASE B: | | |
| Deionized water | qs 100 | qs 100 |
| Sequestering agent | 0.1 | 0.1 |
| Glycerol | 5.0 | 5.0 |
| Xanthan gum | 0.2 | 0.2 |
| Monocetyl phosphate | 1.0 | 1.0 |
| PHASE C: | | |
| Isohexadecane | 1.0 | 1.0 |
| Acrylic acid/stearyl methacrylate copolymer | 0.2 | 0.2 |
| Triethanolamine | qs | qs |

The aqueous phase (Phase B) containing all of its ingredients is heated to 80° C. in a water bath. The fatty phase (Phase A) containing all of its ingredients is heated to 80° C. in a water bath. A is emulsified in B with stirring of rotor-stator type (machine from the company Moritz). Phase C is incorporated and the mixture is allowed to cool to room temperature with moderate stirring. The triethanolamine is introduced so as to adjust the pH to the desired value at the end of manufacture.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological photoprotective composition, comprising:

a) at least one 1,3,5-triazine derivative comprising 2,4-bis{[4-2-ethylhexyloxy)]-2-hydroxy]phenyl}-6-(4-methoxyphenyl)-1,3,5-triazine of the following formula:

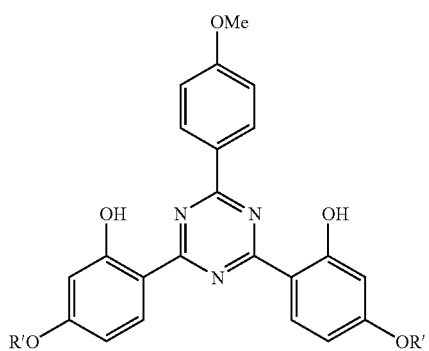

in which R' is a 2-ethylhexyl radical, and
b) a mixture comprising:
(i) at least one amide-based oil comprising isopropyl N-lauroylsarcosinate of formula:

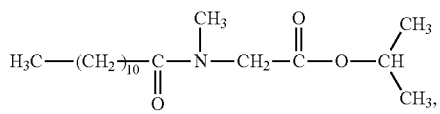

and
(ii) 2-phenylethyl benzoate of the following formula:

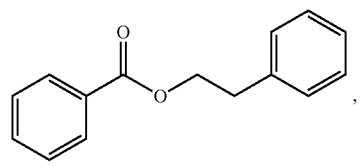

wherein, the composition is formulated into a topically applicable, cosmetically/ dermatologically acceptable medium,
wherein the 2,4-bis{[4-2-ethylhexyloxy)]-2-hydroxy]phenyl}-6-(4-methoxyphenyl)-1,3,5-triazine is present in an amount of from 1.0% to 10%, the isopropyl N-lauroylsarcosinate is present in an amount of from 1% to 20%, and the 2-phenylethyl benzoate is present in an amount of from 1% to 30%, by weight relative to the total weight of the composition,
wherein UV active benzophenone derivatives are not present.

2. The cosmetic/dermatological composition as defined by claim 1, further comprising at least one additional organic photoprotective agent and/or at least one additional mineral photoprotective agent, which is/are water-soluble, liposoluble or insoluble in the cosmetic solvents commonly employed.

3. The cosmetic/dermatological composition as defined by claim 2, comprising at least one additional organic photoprotective agent selected from the group consisting of anthranilates; cinnamic derivatives; salicylic derivatives; camphor derivatives; β,β'-diphenylacrylate derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; dimers derived from α-alkylstyrene; 4,4-diarylbutadienes, and mixtures thereof.

4. The cosmetic/dermatological composition as defined by claim 3, comprising at least one additional organic photoprotective agent selected from the group consisting of:
Homosalate,
Ethylhexyl salicylate,
Ethylhexyl methoxycinnamate,
Octocrylene,
Phenylbenzimidazolesulfonic acid,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Methylenebis(benzotriazolyl)tetramethylbutylphenol,
Drometrizole trisiloxane,
Polysilicone-15,
1,1-Dicarboxy(2,2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine,
and mixtures thereof.

5. The cosmetic/dermatological composition as defined by claim 2, comprising at least one additional mineral photoprotective agent that is a coated or uncoated metal oxide pigment or nanopigment.

6. The cosmetic/dermatological composition as defined by claim 2, comprising at least one additional mineral screening agent that is a nanopigment of titanium oxide, which is amorphous or crystallized in rutile and/or anatase form, or of iron oxide, zinc oxide, zirconium oxide or cerium oxide.

7. The cosmetic/dermatological composition as defined by claim 1, further comprising at least one agent for artificially tanning and/or browning the skin.

8. The cosmetic/dermatological composition as defined by claim 1, further comprising at least one adjuvant selected from the group consisting of fatty substances, organic solvents, ionic or nonionic, hydrophilic or lipophilic thickeners, softeners, humectants, opacifiers, stabilizers, emollients, silicones, antifoams, fragrances, preservatives, anionic, cationic, nonionic, zwitterionic or amphoteric surfactants, active agents, fillers, polymers, propellants and acidifying or basifying agents.

9. The cosmetic/dermatological composition as defined by claim 1, said amide-based oil/arylalkyl benzoate compound admixture being present in an amount that itself is sufficient for dissolving all of the triazine screening agent present in the composition.

10. A process for cosmetically treating or caring for the skin, lips, nails, hair, eyelashes, eyebrows and/or scalp of an individual in need of such treatment, comprising topically applying thereon, a thus effective amount of the cosmetic/dermatological composition as defined by claim 1.

11. A process for photoprotecting the skin, hair, lips and/or scalp against the damaging effects of UV-irradiation, comprising topically applying thereon, a thus effective amount of the cosmetic/dermatological composition as defined by claim 1.

12. A process for enhancing the sun protection factor, cosmetic properties and/or stability of at least one 1,3,5-triazine derivative, comprising formulating therewith a thus effective amount of at least one arylalkyl benzoate compound and at least one amide-based oil to form the composition as defined by claim 1.

13. The cosmetic/dermatological composition as defined by claim 1, formulated as an emulsion, a milk, a gel, a cream, a lotion, a powder, a stick, a mousse, or a spray.

14. A topically applicable cosmetic/dermatological photoprotective composition, consisting essentially of:
   a) 2,4-bis{[4-2-ethylhexyloxy)]-2-hydroxy]phenyl}-6-(4-methoxyphenyl)-1,3,5-triazine of the following formula:

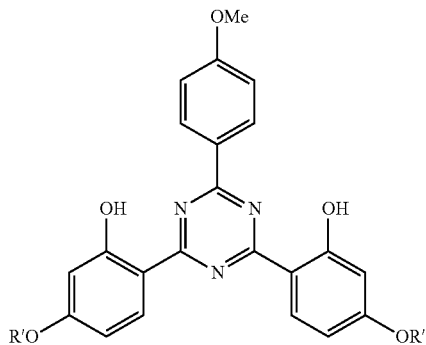

in which R' is a 2-ethylhexyl radical, and
   b) a mixture consisting essentially of:
      (i) isopropyl N-lauroylsarcosinate of formula:

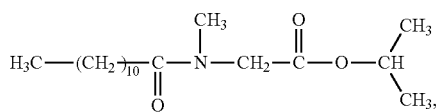

and
      (ii) 2-phenylethyl benzoate of the following formula:

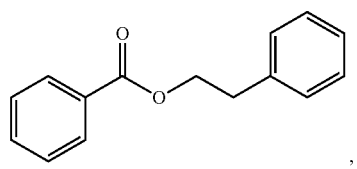

wherein, the composition is formulated into a topically applicable, cosmetically/dermatologically acceptable medium,
wherein the 2,4-bis{[4-2-ethylhexyloxy)]-2-hydroxy]phenyl}-6-(4-methoxyphenyl)-1,3,5-triazine is present in an amount of from 1.0% to 10%, by weight relative to the total weight of the composition,
wherein the isopropyl N-lauroylsarcosinate is present in an amount of from 1% to 20%, by weight relative to the total weight of the composition, and
wherein the 2-phenylethyl benzoate is present in an amount of from 1% to 30%, by weight relative to the total weight of the composition,
wherein UV active benzophenone derivatives are not present.

15. The cosmetic/dermatological composition as defined by claim 14, further consisting essentially of at least one agent for artificially tanning and/or browning the skin.

16. The cosmetic/dermatological composition as defined by claim 1, further comprising at least one organic photoprotective agent and/or at least one mineral photoprotective agent, wherein the at least one organic photoprotective agent and/or at least one mineral photoprotective agent is present in an amount of 0.1% to 10% by weight relative to the total weight of the composition.

17. The cosmetic/dermatological composition as defined by claim 14, further comprising at least one organic photoprotective agent and/or at least one mineral photoprotective agent, wherein the at least one organic photoprotective agent and/or at least one mineral photoprotective agent is present in an amount of 0.1% to 10% by weight relative to the total weight of the composition.

18. The cosmetic/dermatological composition as defined by claim 1, further comprising ethyl N-acetyl-N-butylaminopropionate, N,N-diethyltoluamide, or a combination thereof.

19. The cosmetic/dermatological composition as defined by claim 1, further comprising a self-tanning agent including dihydroxyacetone.

20. The cosmetic/dermatological composition as defined by claim 1, further comprising N,N-diethyltoluamide.

21. The cosmetic/dermatological composition as defined by claim 1, wherein the isopropyl N-lauroylsarcosinate is present in an amount of from 1% to 10%, or the 2-phenylethyl benzoate is present in an amount of from 1% to 10%, by weight relative to the total weight of the composition.

22. The cosmetic/dermatological composition as defined by claim 1, wherein the isopropyl N-lauroylsarcosinate is present in an amount of from 1% to 10%, and the 2-phenylethyl benzoate is present in an amount of from 1% to 10%, by weight relative to the total weight of the composition.

* * * * *